United States Patent [19]

Suga

[11] 4,021,713

[45] May 3, 1977

[54] APPARATUS FOR SEQUENTIAL MEASUREMENT OF LIGHT TRANSMITTED THROUGH SMOKE

[76] Inventor: Shigeru Suga, Yoyogi 5-20-2, Shibuya, Tokyo, Japan

[22] Filed: Mar. 29, 1976

[21] Appl. No.: 671,700

[52] U.S. Cl. .............................. 250/574; 250/233; 356/207; 356/205; 340/23.7 S

[51] Int. Cl.² ..................... G01D 5/36; G01N 21/26

[58] Field of Search ......... 250/564, 565, 573, 574, 250/575, 232, 233; 356/207, 205; 340/237 S

[56] References Cited

UNITED STATES PATENTS

| | | | |
|---|---|---|---|
| 2,877,453 | 3/1959 | Mendenhall, Jr. | 340/237 S |
| 3,885,162 | 5/1975 | Geertz | 356/207 |
| 3,897,154 | 7/1975 | Hawes | 250/575 |

*Primary Examiner*—Alfred E. Smith
*Assistant Examiner*—David K. Moore
*Attorney, Agent, or Firm*—Wenderoth, Lind & Ponack

[57] ABSTRACT

An apparatus for continuous and sequential measurement of amounts of reflected, diffused and directly transmitted light transmitted through smoke. The apparatus has a smoke chamber having a smoke introduction port and a smoke discharge port, and further has an aperture in one wall thereof. A first light source is aligned with the aperture, and a first sector member having an aperture therein.

A light receiving device is disposed on another wall of the smoke chamber opposite the aperture in the one wall, and a light measuring circuit is coupled to the light receiving device.

A second light source in the smoke chamber is directed toward the aperture in the one wall to strike the first sector member at an angle to the surface thereof, and a second sector member is rotatably mounted in the smoke chamber for movement between the second light source and the aperture in the one wall and has an aperture therein for alignment with the second light source. Sector member driving means connected to the sector members drives them in synchronization for aligning the aperture in the second sector member with the second light source when white reflection and black reflection portions of the first sector member are aligned with the aperture in the one wall, and for aligning the remainder of the second sector member with the second light source when the aperture in the first sector member is aligned with the first light source and the aperture in the one wall.

6 Claims, 6 Drawing Figures

APPARATUS FOR SEQUENTIAL MEASUREMENT OF LIGHT TRANSMITTED THROUGH SMOKE

This invention relates to an apparatus for measurement of certain characteristics of smoke which is generated when a sample of a material is burned in a combustion analyzer or like apparatus, and provides an apparatus for continuously measuring the transmissibility characteristic of the smoke with respect to three types of light, namely reflected, diffused and directly transmitted light.

BACKGROUND OF THE INVENTION AND PRIOR ART

Heretofore, measurement of the characteristics of smoke has been carried out by determining the transmissibility of the smoke with respect to directly transmitted light. In addition, measurement has been made of smoke characteristics by measuring transmissibility of reflected light. However, in order to carry out both measurements, two optical systems must be provided, one for each type of measurement. In this arrangement, either the light source for measuring the directly transmitted light characteristic or the one for measuring the reflected light characteristic must be turned off when the other is turned on, otherwise the light from the two sources interfere with each other. When measurements of the directly transmitted and reflected light characteristics are conducted repeatedly, therefore, the lamps constituting the respective light sources must be turned on and off repeatedly.

Moreover, the quantity of light emitted by a lamp is generally not the same immediately after it is turned on as it is after a certain lapse of time, so that the quantity of light in the above-described conventional apparatus varies corresondingly. For this reason, the values measured by the apparatus have inherently poor accuracy.

OBJECT AND SUMMARY OF THE INVENTION

It is an object of the present invention to provide an apparatus which overcomes these drawbacks and in which the lamps of the light source can be kept on at all times. This object is achieved by an apparatus according to the invention for continuous and sequential measurement of amounts of reflected, diffused and directly transmitted light transmitted through smoke, said apparatus comprising:

a smoke chamber having a smoke introduction port and a smoke discharge port, and further having an aperture in one wall thereof;

a first light source aligned with said aperture, and a first sector member having an aperture therein, a white reflection portion and a black reflection portion spaced therearound and rotatably mounted for movement between said one chamber wall and said first light source for alignment of said aperture and said portions with said aperture in said one wall;

a light receiving device disposed on another wall of said smoke chamber opposite said aperture in said one wall, and a light measuring circuit coupled to said light receiving device;

a second light source in said smoke chamber directed toward said aperture in said one wall to strike said first sector member at an angle to the surface thereof, and a second sector member rotatably mounted in said smoke chamber for movement between said second light source and said aperture in said one wall and having an aperture therein for alignment with said second light source; and sector member driving means connected to said sector members for driving them in synchronization for aligning the aperture in said second sector member with said second light source when the white reflection and black reflection portions of said first sector member are aligned with said aperture in said one wall, and for aligning the remainder of said second sector member with said second light source when the aperture in said first sector member is aligned with said first light source and said aperture in said one wall.

DETAILED DESCRIPTION OF THE INVENTION

Figure 1:
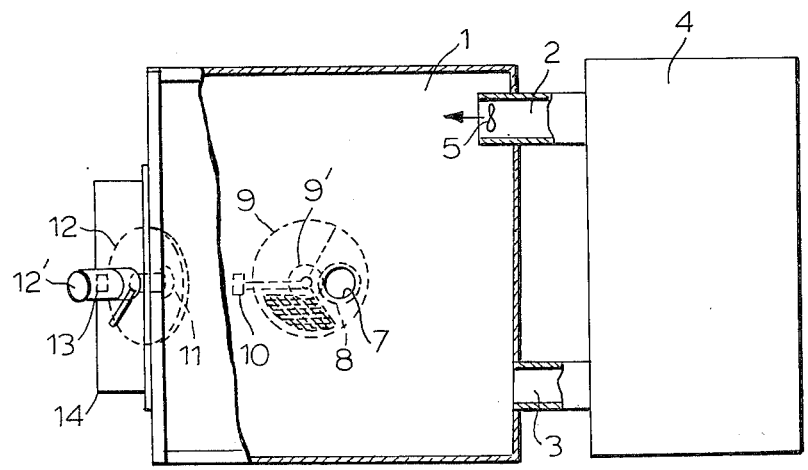
FIG. 1 is a partially cut away sectional side view of the apparatus according to the present invention.
Figure 2:
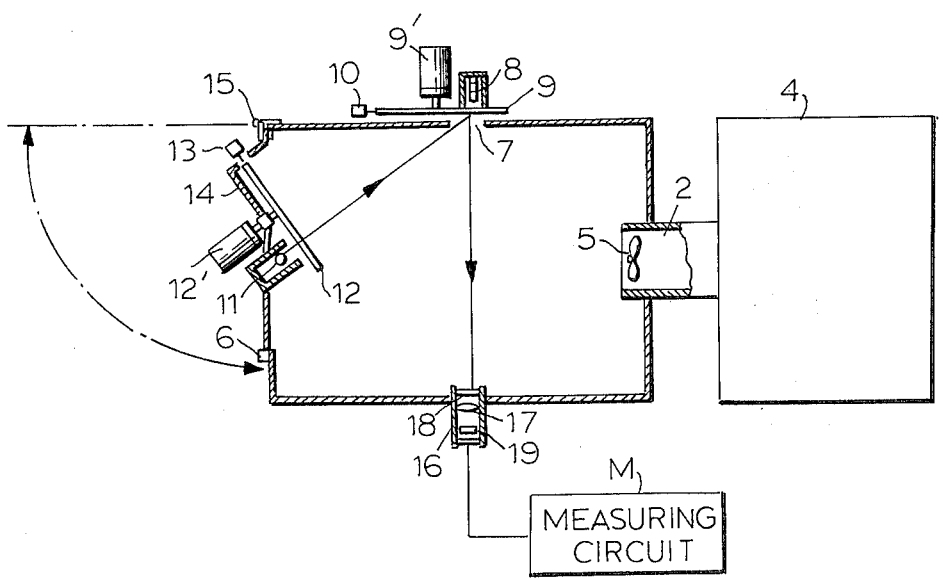
FIG. 2 is a sectional plan view of the apparatus shown in FIG. 1.

Referring now to the accompanying drawings, as illustrated in FIGS. 1 and 2, a smoke chamber 1 made of metal plate has a smoke introduction port 2 and a smoke discharge port 3, each being disposed in one side wall of chamber 1 and connected to an external smoke generating section 4 such as a combustion analyzer, for example. The smoke generated by the smoke generating section 4 is introduced into the smoke chamber 1 by means of a fan 5 in introduction port 2.

An aperture 7 is provided in another side wall of the smoke chamber 1, and has a light source lamp 8 aligned therewith for emitting light for measurement of directly transmitted light characteristics. A sector member 9, a motor 9' on which the sector member is mounted for being driven by motor 9', and a control switch 10 adjacent the path of rotation of the sector member are provided adjacent aperture 7. The sector member 9 is positioned to pass between lamp 8 and aperture 7 when it is rotated by motor 9'.

A light source lamp 11 for providing light for measurement of reflected light characteristics, a sector member 12 and a control switch 13 for the sector member 12 are mounted on a panel 14 which is pivotally mounted on a side wall of the smoke chamber 1 by a hinge 15 so as to be swung out of the chamber 1 to facilitate maintenance and cleaning of the apparatus.

Figures 3, 4:
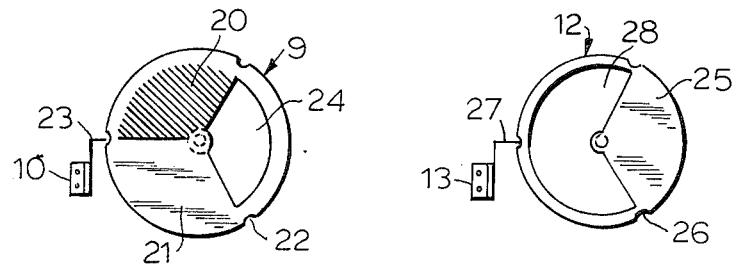
FIG. 3 is a diagrammatic view of a sector A.
FIG. 4 is a diagrammatical view of the sector B.

FIG. 3 illustrates the sector member 9 which is constituted by a disc having a sector shaped aperture therein with a center angle of about 120° and the sector shaped portions 20 and 21 thereon a black reflection portion 20 and a white reflection portion 21, respectively, each portion having a center angle of about 120°. The disc has three notches 22 in the periphery thereof engaged by a lever 23 of the switch 10 for controlling the rotation of the sector at each one-third of a rotation.

FIG. 4 illustrates the sector 12 which the constituted by a disc 25 having a sector-shaped aperture 28 therein with a center angle of 240°, and which has notches 26 with which lever 27 of switch 13 cooperates.

Figure 6:
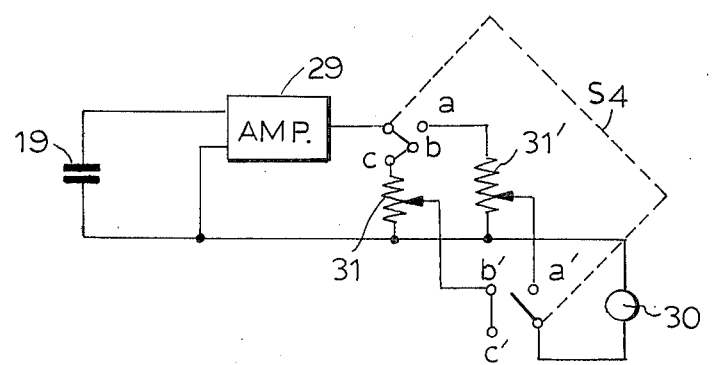
FIG. 6 is a circuit diagram of a measuring circuit.

A light receiving device consists of a lens 17, a glass filter 18, and a photoelectric cell 19, and is connected to an external measuring circuit M. Measurement of the amount of light received is made by means of a meter, a recorder and the like. FIG. 6 shows the measuring circuit.

In the measuring circuit, the photoelectric current from the photoelectric cell 19 is applied to the input of an amplifier 29. When contacts of switch $S_4$ are in the switching positions a and a', the output of the amplifier 29 is connected to a variable resistor 31'. Likewise when the switch $S_4$ has the contacts in the positions of b and b' or c and c', the amplifier is connected to a variable resistor 31.

The switch $S_4$ consists of two gang switches with the contacts a, b and c being interlocked with the contacts a', b' and c'. The contact element on the side of the contacts a', b' and c' is connected to a meter 30.

The variable resistor 31' is connected for measurement of directly transmitted light while the variable resistor 31 is used for measurement of transmitted diffused and reflected light. The switch $S_4$ is a rotary-type switch responsive to the rotation of the rotary shaft of the sector member 9. After the variable resistors 31 and 31' are properly adjusted, smoke is introduced into chamber 1 for the taking of measurements.

Light travels through the chamber 1 along the paths indicated by the arrows in FIG. 2 from the light sources, through the sector shaped openings to the light receiving device. To carry out measurement of the amount of reflected light transmitted through the smoke, the sector member 9 is positioned with the white reflection portion 21 aligned with hole 7 and sector member 12 is positioned with aperture 28 aligned with light source 11. Light from the light source 11 passes through the aperture 28 of the sector member 12 and strikes white reflection portion 21 of the sector member 9. Light reflected in the vertical direction to sector member 9 is received by the photoelectric cell 19. After smoke is introduced, measurement of the light received is effected with the reference value being 100 at the time when the smoke is absent.

When the sector members 9 and 12 are turned one-third of a rotation, the light from the light source 11 still passes through the aperture 28 of the sector member 12 and strikes the black reflection portion 20 of the sector member 9. The diffused light transmitted from sector member 9 through the smoke particles is received and measured by the photoelectric cell 19.

In order to effect measurement of directly transmitted light, the sectors A and B are further turned one-third of a rotation so that the light from the light source 11 is intercepted by the sector member 12, and the light from the light source 8 passes through the aperture 24 of the sector member 9. The thus directly transmitted light is received by the photoelectric cell 19. After the smoke is introduced, measurement is effected likewise with the reference value being 100 at the time when the smoke is absent.

Figure 5:
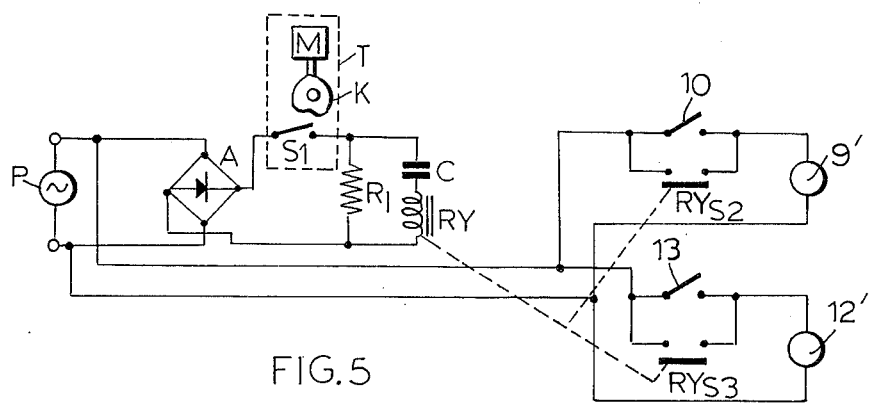
FIG. 5 is a circuit diagram of a circuit which interlocks and controls the sectors shown in FIGS. 3 and 4.

The abovedescribed measurements of reflected and diffused light transmitted through the smoke, and light directly transmitted are conducted in sequence periodically and continuously by means of a control circuit which is illustrated in FIG. 5.

The control circuit periodically rotates the sector members 9 and 12 one-third of a rotation (for example, every 30 seconds). The circuit comprises an a.c. power supply P, a rectifier A, a timer T equipped with a contact $S_1$, and a series connected capacitor C and relay $R_y$. A resistor $R_1$ is connected between one end of the capacitor C and the other end of the relay $R_y$.

The relay $R_y$ controls contacts $R_{ys2}$ and $R_{ys3}$, which are respectively connected between the power supply P and motors 9' and 12' in parallel with switches 10 and 13, which are mechanically opened when the levers 23 and 27 enter notches 22 and 26 in the edges of the sector members.

The timer T consists, for example, of a synchronous motor $M_1$ driving a cam K acting on the switch $S_1$ to close it at predetermined intervals of time. When the switch $S_1$ is closed, a d.c. voltage is impressed between C and $R_y$, whereby the capacitor C is charged and actuates the relay $R_y$ to close the contacts $R_{ys2}$ and $R_{ys3}$. Each when the switch $S_1$ is opened to cut off the connection with the power supply, the relay $R_y$ remains energized for a period corresponding to the discharge time of the capacitor during which the electric charge on the capacitor is discharged through the resistor $R_1$ and the relay $R_y$.

Accordingly, a proper selection of the values for C and $R_1$ makes it possible to locate the levers 23 and 27 in the grooves of the sector members while the sector members are stopped and keep the switches 10 and 13 opened.

Upon actuation of the relay $R_y$, the motors 9' and 12' for the sector members 9 and 12 are actuated, and the levers are moved out of the notches in the sector members, thereby closing switches 10 and 13. Next, the relay $R_y$, which has been energized only for the period of time corresponding to the discharge time of the capacitor is deenergized. Since the switches 10 and 13 are mechanically closed in this instance, however, the motors keep operating until the levers 23 and 27 drop into the subsequent notches.

In the meantime, the contact $S_1$ of the timer having opened, thereby interrupting the supply of the current to the capacitor C, and the electric charge stored in the capacitor having been discharged through the resistor $R_1$, the circuit is ready for a repetition of the operation. The next actuation of the time switch $S_1$ starts the operation again.

In carrying out the measurement in the present apparatus, before the smoke is introduced, the measuring circuit is adjusted so that the quantities of reflected and directly transmitted light produce a meter reading of 100. After the sector control circuit is energized, the smoke is introduced into the apparatus. Measured values of light transmitted through the smoke are indicated by the meter 30 every interval of time in the order of reflected light, diffused light, and directly transmitted light. At the initial stage of combustion, the value for reflected light is less than 100, and apparently different from the value of reflected light for the fuming smoke produced at the time of extinguishing the combustion. Thus, the values for the smoke can be measured throughout the entire course of the combustion.

What is claimed is:
1. An apparatus for continuous and sequential measurement of amounts of reflected, diffused and directly transmitted light transmitted through smoke, said apparatus comprising:
   a smoke chamber having a smoke introduction port and a smoke discharge port, and further having an aperture in one wall thereof;

a first light source aligned with said aperture, and a first sector member having an aperture therein, a white reflection portion and a black reflection portion spaced therearound and rotatably mounted for movement between said one chamber wall and said first light source for alignment of said aperture and said portions with said aperture in said one wall;

a light receiving device disposed on another wall of said smoke chamber opposite said aperture in said one wall, and a light measuring circuit coupled to said light receiving device;

a second light source in said smoke chamber directed toward said aperture in said one wall to strike said first sector member at an angle to the surface thereof, and a second sector member rotatably mounted in said smoke chamber for movement between said second light source and said aperture in said one wall and having an aperture therein for alignment with said second light source; and sector member driving means connected to said sector members for driving them in synchronization for aligning the aperture in said second sector member with said second light source when the white reflection and black reflection portions of said first sector member are aligned with said aperture in said one wall, and for aligning the remainder of said second sector member with said second light source when the aperture in said first sector member is aligned with said first light source and said aperture in said one wall.

2. An apparatus as claimed in claim 1 further comprising a smoke generating section connected to said smoke introduction port.

3. An apparatus as claimed in claim 1 in which the side of the smoke chamber opposite the side in which said smoke introduction port is located in a panel hinged to said smoke chamber for swinging movement out of the chamber, said second sector member and second light source being mounted on said panel.

4. An apparatus as claimed in claim 1 in which said sector member driving means comprises a motor coupled to each sector member and a control circuit coupled to said motors for driving said motors.

5. An apparatus as claimed in claim 4 in which said control circuit comprises means for connection to an A.C. power supply, a timer switch means having a synchronous motor and a switch member actuated by said motor, a rectifier means connected between said power supply connection means and said switch member, a capacitor and a relay connected in series and coupled to said switch member, a resistor coupled in parallel with said capacitor and relay, motor control switches connected between said power supply connection means and said motors, and a relay contact means connected in parallel with said motor control switches and actuated to the closed position by energization of said relay, said motor control switches being mechanically coupled to said sector members for actuation thereby to the closed condition during rotation between positions of the sector members and to the open position when the sector members reach the desired positions.

6. An apparatus as claimed in claim 1 wherein said light receiving device comprises a photoelectric cell, and said measuring circuit comprises an amplifier coupled to said photoelectric cell, a pair of variable resistors, a meter, and a rotary switch having two three-contact switching members, one of the switching members being coupled to said amplifier, the first contact of said one switching member being coupled to one of the variable resistors and the other contacts thereof being coupled to the other of the variable resistors, and the other switching member being coupled to the amplifier through said meter and one of the contacts thereof being coupled to the movable contact of the one variable resistor and the other contacts thereof being coupled to the movable contact of the other variable resistor.

* * * * *